United States Patent [19]

Burton

[11] Patent Number: 4,898,681

[45] Date of Patent: Feb. 6, 1990

[54] HYPOCHLORITE DISINFECTANT STABILIZED WITH CALCIUM CHELANT

[76] Inventor: Charles D. Burton, 3807 Chestnut Hill Dr., Midland, Mich. 48640

[21] Appl. No.: 238,466

[22] Filed: Aug. 31, 1988

[51] Int. Cl.$^4$ .............. D06L 3/08; C11D 3/395; A61L 2/16; A01N 33/04

[52] U.S. Cl. .................. 252/102; 252/186.37; 252/186.36; 252/187.25; 252/187.26; 252/550; 252/106

[58] Field of Search .......... 252/186.37, 186.36, 252/187.25, 187.26, 102

[56] References Cited

U.S. PATENT DOCUMENTS

| | | | |
|---|---|---|---|
| 2,698,823 | 1/1955 | Bersworth et al. | 167/68 |
| 2,988,514 | 6/1961 | Robson et al. | 252/102 X |
| 3,170,883 | 2/1965 | Owen et al. | 252/102 X |
| 4,011,172 | 3/1977 | Marsan et al. | 252/187.26 X |
| 4,071,463 | 1/1978 | Steinhauer | 252/103 |
| 4,164,477 | 8/1979 | Whitley | 252/99 |
| 4,259,200 | 3/1981 | Sims et al. | 252/102 |
| 4,287,080 | 9/1981 | Siklosi | 252/104 |
| 4,302,350 | 11/1981 | Callicott | 252/174.23 |
| 4,497,725 | 2/1985 | Smith et al. | 252/102 |

OTHER PUBLICATIONS

MMWR, Morbidity and Mortality Weekly Report, Aug. 21, 1987 p. 10S.
The Dow Chemical Company "Keys to Chelation", 1980 pp. 1.5, 1.6, 2.15, 2.16, 6.3 A Looseleaf catalog of the VERSENE family of chelating agents.

Primary Examiner—Brooks H. Hunt
Assistant Examiner—Virginia B. Caress
Attorney, Agent, or Firm—William Miller Yates

[57] ABSTRACT

Dilute aqueous sodium hypochlorite solution is stabilized against decomposition during storage by incorporating in it a small proportion of the calcium chelate of disodium ethylenediaminetetraacetic acid. The solution preferably contains by weight at least 95 percent water, from 0.25 to 1 percent sodium hypochlorite, and from 0.005 to 0.25 percent of the calcium chelate. It may be stored for a period of many months and remains effective as a disinfectant for medical environmental surfaces. The solution may also be formulated to contain a synthetic detergent, such as sodium lauryl sulfate, 0.1 to 3 percent, and an alkaline builder, such as sodium metasilicate, to maintain a pH value above 11. Sodium hydroxide may be added to produce a pH above 12.

8 Claims, No Drawings

HYPOCHLORITE DISINFECTANT STABILIZED WITH CALCIUM CHELANT

TECHNICAL FIELD

This invention relates to aqueous sodium hypochlorite disinfectant or bleach solutions stable against decomposition during storage. It particularly concerns dilute sodium hypochlorite disinfectant solution containing a specific calcium chelate which maintains the solution at nearly full strength over many months.

BACKGROUND OF THE INVENTION

Commercially available sodium hypochlorite solution (household bleach) is an inexpensive germicide. Diluted 1;10 with water, or even 1:100, it is effective against many disease organisms. The 1:10 dilution meets Center for Disease Control (CDC) recommendations for an AIDS virus disinfectant, acting to kill the virus on laboratory and other work surfaces in as little as one minute.

However, there is a practical problem in that such dilutions can quickly lose strength. Current recommendations are to prepare solutions fresh daily. Such replacement is inconvenient and adds considerable expense when spray bottles or other containers of disinfectant are to be kept continuously ready at several work locations. The present invention is directed to avoiding this problem by providing a dilute hypochlorite disinfectant solution which retains virtually full strength over a year or more.

In the past, various additives and formulations for stabilizing dilute sodium hypochlorite have been tried. (For a listing, see U.S. Pat. No. 4071463.) While some of these may help, even the more effective known formulations provide a stability at room temperature measured by a halflife of at most a few months. This, though adequate for many purposes, falls far short of providing a degree of stability optimum for laboratory disinfectants intended to be shelved in containers for a long period and then put in service and dispensed repeatedly in daily use. For this purpose, the disinfectant should retain at least 75 percent of its hypochlorite content for a period of many months, even years.

Another difficulty with known stabilized dilute hypochlorite disinfectants is that the stabilization has been unreliable, sometimes differing significantly from batch to batch. This variation is attributed, though not with certainty, to the random but nearly unavoidable presence of heavy metal ions in varying trace amounts (parts per million) in the water sources and containers used in formulating and storing the hypochlorite. Such ions, e.g. copper, nickel, and cobalt, are known to accelerate the decomposition of hypochlorite. It is difficult to exclude minute traces of them reliably and completely from formulations, even by conventional deionization of the diluent water, since contact with metal surfaces during manufacture or with impurities in formulative additives can provide ingress of heavy metals. It has been proposed that adding a chelating agent to the water source or disinfectant formulations may improve hypochlorite life by deactivating whatever trace heavy metal ions may be present. Unfortunately, hypochlorite is a sufficiently strong oxidizing agent that it degrades most available chelating agents, making them ineffective.

To summarize, stabilization of dilute hypochlorite bleach to an extent adequate to provide a long-lived laboratory disinfectant has continued as a largely unsolved problem.

SUMMARY OF THE INVENTION

In the invention, dilute aqueous sodium hypochlorite solution is stabilized against decomposition during storage by incorporating in it a small proportion of the calcium chelate of disodium ethylenediaminetetraacetic acid. Thus stabilized, even at high dilutions, the hypochlorite retains nearly its initial strength for many months. When intended for disinfecting surfaces on which considerable organic matter is present, the diluted hypochlorite may be formulated to contain also a synthetic detergent and an alkaline builder.

DETAILED DESCRIPTION

Sodium hypochlorite, supplied in standard commercial strength, contains 12 to 13 percent by weight NaOCl. This can be modified to give commercial household bleach of 5 to 6 percent NaOCl. Both strengths can be diluted with water to a concentration no more than 3 percent for use as disinfectant and mild bleach. This lesser strength range is termed herein as "dilute" hypochlorite. Concentrations of 0.25 to 1 percent NaOCl, usually over 0.5 percent, better about 0.65 percent, are preferred as medical and environmental surface disinfectants. It is in this latter use that there arises the difficult problem of loss of strength on storage, often rapid.

In the present invention, dilute aqueous sodium hypochlorite solution is stabilized against decomposition by incorporating in it a small but effective proportion of the calcium chelate of disodium ethylenediaminetetraacetic acid. This action as a stabilizer appears to be unique to this particular chelating agent, not shared by other chelants closely related chemically. Unusual also, and essential to the present invention, is the fact that this calcium chelate is not degraded during storage by the oxidizing action of the hypochlorite.

The calcium chelate of disodium ethylenediaminetetraacetic acid is an article of commerce, available under the trademark VERSENE CA. Its preparation is described, for example, in U.S. Pat. No. 2,698,823. Supplied as a white crystalline powder (the dihydrate), it is used in food technology. It is often called "calcium disodium EDTA". For convenience, the quoted term will be used hereinafter.

Only a small proportion of calcium disodium EDTA is needed to stabilize dilute aqueous sodium hypochlorite against decomposition on storage. From about 0.005 to 0.25 percent by weight of the total hypochlorite solution is usually sufficient, unless there is gross heavy metal contamination. The range 0.01 to 0.02 percent is preferred.

In formulating disinfectant according to the invention, industrial bleach is first diluted with water to the desired strength, e.g. 0.65 percent NaOCl. Calcium disodium EDTA, as crystals or dispersed in water, is stirred in to the desired concentration, such as 0.01 to 0.02 percent. The dilute hypochlorite thus stabilized can be formulated with a detergent and builder and then packaged in closed containers from which portions may be dispensed as wanted. The water source is preferably one as nearly free of heavy metal ions as convenient, e.g. deionized or distilled water. However, an advantage of the invention is that extreme caution need not be taken with respect to minimizing heavy metal ion content. Tap water or well water will usually suffice. Likewise, while storage in all-glass or -plastic storage containers is preferred, the formulated hypochlorite will retain its stability even when the packaging involves exposure to some metal, as bottle caps, sprayer parts, etc. Additionally, during formulation contact with all metals need not be scrupulously avoided. A particularly desirable feature is that aqueous hypochlorite or its formulations made according to the invention are uniformly stable, i.e. do not vary unpredictably in stability from batch to batch. Stability is, of course, optimum when the formulations are made up, stored, shipped, and used at room temperature.

In using the dilute stabilized hypochlorite of the invention, it is simply applied in conventional manner to medical and other environmental surfaces to be disinfected. An adequate portion is dispensed from the storage container and swabbed or sprayed on the laboratory, laundry, or kitchen surfaces to be treated.

The effectiveness of dilute sodium hypochlorite as a disinfectant may be diminished when the surface to be treated has on it gross organic matter, such as blood or mucus. In formulating disinfectant to be used on such surfaces, it is desirable to include in the solution a synthetic detergent stable in the presence of hypochlorite. The detergent helps the solution to penetrate the soil. Such detergents are well known. The criteria for selecting them are set forth in U.S. Pat. No. 4,071,463. Sodium lauryl sulfate is preferred, added in a concentration of from about 0.1 to about 3 percent by weight of the solution.

Further advantage, in formulating a stabilized hypochlorite disinfectant for use with organic soil may be realized by incorporating in the solution a soluble alkaline builder in a proportion sufficient to maintain a pH value above about 11. Builders satisfactory for this purpose are detailed in U.S. Pat. No. 4,071,463. Sodium metasilicate is especially effective, helping also to minimize corrosion of metal articles, such as surgical instruments, dipped in the hypochlorite for disinfection.

When conditions of extreme soil are to be encountered, it is advantageous to include in the hypochlorite solution sodium hydroxide in a proportion sufficient to maintain a pH value above about 12.

For an all-purpose dilute hypochlorite disinfectant stabilized according to the invention, the following recipe is very satisfactory: deionized water, at least 95 percent by weight; sodium hypochlorite, 0.5 to 1 percent; calcium disodium EDTA, 0.01 to 0.02 percent; sodium lauryl sulfate, 0.1 to 1 percent; sodium metasilicate, 0.1 to 1 percent; and sodium hydroxide, about 0.1 percent (to maintain a pH of at least 12). If desired, there may also be added a fragrance stable to hypochlorite. This formulation, in a glass or plastic container, retains at least 75 percent of its initial hypochlorite strength, often 85 percent, for two years or more.

This stability provides sufficient time for several containers of the formulation to be sold in a group, as in cartons, and shelved at distribution centers for months before the containers are put in individual use. Storage of this duration has heretofore been unknown with dilute aqueous hypochlorite disinfectant.

EXAMPLE

A series of laboratory runs was made to compare the stability on aging of several hypochlorite solutions identical in initial hypochlorite content but containing different agents being tested as stabilizers.

All runs used the same basic formulation prepared by mixing one part of a high-quality commercial sodium hypochlorite bleach with seventeen parts of deionized water. Formulation was completed by adding sodium lauryl sulfate, sodium metasilicate, sodium hydroxide, and perfume in proportions as stated above. It contained about 0.57 percent NaOCl. (The hypochlorite concentration was determined conventionally by titrating with sodium thiosulfate the free iodine released on mixing the hypochlorite solution with potassium iodide.)

The runs were carried out in 660 ml polyethylene bottles closed with plastic finger pumps which had stainless steel balls and springs. The bottles were stored at a temperature of about 25° C. The NaOCl content of the formulation in each bottle was analyzed at the start of each run and again at intervals throughout the storage period.

In Run 1, to the basic aqueous hypochlorite formulation there was added 0.1 gram (0.015 percent) calcium disodium EDTA (VERSENE CA) as stabilizer. Run 2 was made with a ten-fold larger quantity of the VERSENE CA, 1.0 gram (0.15 percent). In Run 3, the additive was 0.1 gram of crystalline VERSENE 220 Crystals, tetrasodium EDTA, a widely used chelant. In Run 4, 1.0 gram of Versene 220 Crystals was added. Run 5 was a control, containing only the basic hypochlorite formulation, no additive.

The results are summarized in the following table, in which the NaOCl content of each run is shown at each of several time intervals.

TABLE

| Days | Run 1 | 2 | 3 | 4 | 5 |
| --- | --- | --- | --- | --- | --- |
| 1 | 0.562 | 0.564 | 0.556 | 0.491 | 0.569 |
| 12 | 0.562 | 0.561 | 0.523 | 0.073 | 0.547 |
| 20 | 0.559 | 0.561 | — | — | 0.532 |
| 32 | 0.558 | 0.556 | — | 0.025 | 0.518 |
| 74 | 0.556 | 0.557 | 0.501 | — | 0.497 |
| 102 | 0.553 | 0.555 | 0.492 | — | 0.482 |
| 152 | 0.550 | 0.553 | 0.460 | — | 0.460 |
| 229 | 0.544 | 0.549 | 0.398 | — | 0.429 |
| 292 | 0.537 | 0.542 | 0.350 | — | 0.393 |

It will be noted that the stability in Runs 1 and 2 is closely similar. In both, the calcium disodium EDTA is highly effective, about equally so at 0.015 and 0.15 percent concentrations. After 292 days (nearly 10 months) the hypochlorite strength remained at 96 percent of the initial value. By extrapolation, the time before strength falls to 75 percent appears to be several years. In contrast, in the blank Run 5, hypochlorite strength declined to the 96 percent level in between 12 and 20 days; after 292 days it was only 69 percent. In Run 3, with tetrasodium EDTA, the drop in strength was even greater than in the blank, with the 96 percent level passed before 12 days. At 292 days the strength was only 63 percent. In Run 4, with a ten-fold increase in tetrasodium EDTA content, strength life was very brief, indicating the susceptibility of his chelant to oxidation by sodium hypochlorite.

The Example shows that the stabilizing action of calcium disodium EDTA on dilute aqueous hypochlorite cannot be attributed simply to the fact that it is a chelating agent for trace heavy metal ions, if any, in the hypochlorite and the diluent water. The closely related additive, tetrasodium EDTA, at least equally strong as a chelant, had a destructive effect on the hypochlorite. The unique effectiveness of calcium disodium EDTA as a stabilizer is readily apparent, but the reasons for its effectiveness are obscure. If its activity as a chelating agent is partly correct as an explanation of its effectiveness, it also seems that an equally important factor is that the calcium chelate is uniquely resistant to the oxidizing action of the hypochlorite.

I claim as my invention:

1. A dilute aqueous sodium hypochlorite solution stabilized against decomposition during storage consisting essentially of dilute aqueous sodium hypochlorite and a small but effectively stabilizing proportion of the calcium chelate of disodium ethylenediaminetetraacetic acid.

2. A disinfectant solution consisting essentially of at least about 95 percent by weight of water, from about 0.25 to about 1 percent of sodium hypochlorite as active disinfectant, and from about 0.005 to about 0.25 percent of the calcium chelate of disodium ethylenediaminetetraacetic acid to stabilize the hypochlorite against decomposition during storage.

3. A disinfectant according to claim 2 also containing a synthetic detergent stable in the presence of hypochlorite.

4. A disinfectant according to claim 3 in which the detergent is sodium lauryl sulfate in a concentration of from about 0.1 to about 3 percent.

5. A disinfectant according to claim 3 also containing a soluble alkaline builder in a proportion sufficient to maintain a pH value above about 11.

6. A disinfectant according to claim 5 in which the builder is sodium metasilicate.

7. A disinfectant according to claim 5 also containing sodium hydroxide in a proportion sufficient to maintain a pH value above about 12.

8. A disinfectant stabilized against decomposition on storage consisting essentially of the following components in approximate proportions by weight: deionized water, at least 95 percent; sodium hypochlorite, 0.5 to 1 percent; the calcium chelate of disodium ethylenediaminetetraacetic acid, 0.01 to 0.02 percent; sodium lauryl sulfate, 0.1 to 1 percent; sodium metasilicate, 0.1 to 1 percent; and a sodium hydroxide, about 0.1 percent (to maintain a pH value of at least 12).

* * * * *